(12) United States Patent
Johnson

(10) Patent No.: US 11,863,609 B2
(45) Date of Patent: Jan. 2, 2024

(54) SYSTEM FOR STORING, PROCESSING, AND ACCESSING MEDICAL DATA

(71) Applicant: Tim Donald Johnson, Norwalk, IA (US)

(72) Inventor: Tim Donald Johnson, Norwalk, IA (US)

(*) Notice: Subject to any disclaimer, the term of this patent is extended or adjusted under 35 U.S.C. 154(b) by 0 days.

(21) Appl. No.: 17/589,939

(22) Filed: Feb. 1, 2022

(65) Prior Publication Data

US 2022/0159095 A1  May 19, 2022

Related U.S. Application Data

(63) Continuation of application No. 16/936,684, filed on Jul. 23, 2020, now Pat. No. 11,277,497.

(60) Provisional application No. 62/879,876, filed on Jul. 29, 2019.

(51) Int. Cl.
| | |
|---|---|
| *H04L 67/01* | (2022.01) |
| *G16H 10/60* | (2018.01) |
| *H04L 9/06* | (2006.01) |
| *H04L 67/133* | (2022.01) |

(52) U.S. Cl.
CPC ............ *H04L 67/01* (2022.05); *G16H 10/60* (2018.01); *H04L 9/0637* (2013.01); *H04L 67/133* (2022.05)

(58) Field of Classification Search
CPC ..... H04L 67/01; H04L 67/133; H04L 9/0637; H04L 9/0897; H04L 9/3239; H04L 9/3297; H04L 9/50; H04L 63/0807; H04L 63/0892; G16H 10/60; G16H 20/10

See application file for complete search history.

(56) References Cited

U.S. PATENT DOCUMENTS

| | | | | |
|---|---|---|---|---|
| 10,586,617 | B1* | 3/2020 | McNair | G16H 50/30 |
| 2003/0236747 | A1* | 12/2003 | Sager | G06Q 20/357 |
| | | | | 705/40 |
| 2004/0030704 | A1* | 2/2004 | Stefanchik | G10L 15/26 |
| 2004/0103062 | A1* | 5/2004 | Wood | G16H 10/65 |
| | | | | 705/41 |
| 2006/0230286 | A1* | 10/2006 | Kitada | G06F 21/34 |
| | | | | 713/186 |

(Continued)

*Primary Examiner* — John M MacIlwinen

(74) *Attorney, Agent, or Firm* — BrownWinick Law Firm; Christopher A. Proskey

(57) ABSTRACT

A system is disclosed for storage, processing, and accessing of data. The system includes a front end system and a back end system communicatively connected to the front end system. A front end system is configured to provide one or more user interfaces configured to store, process, and access data in a first data server, in response to user input, by sending messages to the back end system. The back end system includes the first data server and one or more processing servers. The one or more processing servers are configured to process messages received from the front end system by accessing in the first data server to perform one or more operations specified by the messages. The back end system also includes a blockchain server configured to maintain a record of changes made to data in the first data server by the one or more processing servers.

18 Claims, 11 Drawing Sheets

(56) References Cited

U.S. PATENT DOCUMENTS

2007/0027715 A1\* 2/2007 Gropper ................ G16H 50/20
                                                    705/2
2014/0236635 A1\* 8/2014 Liberty ................ G16H 10/60
                                                    705/3

\* cited by examiner

SYSTEM FOR STORING, PROCESSING, AND ACCESSING MEDICAL DATA

CROSS REFERENCE TO RELATED APPLICATION

This application is a continuation of U.S. patent application Ser. No. 16/936,684 filed on Jul. 23, 2020, which claims benefit of U.S. Provisional Patent Application No. 62/879,876 which was filed on Jul. 29, 2019, the entirety of each is hereby fully incorporated by reference herein.

FIELD OF THE DISCLOSURE

This disclosure relates generally to data networking and processing. More specifically, and without limitation, this disclosure is directed to systems and methods for storing managing medical data and transactions.

OVERVIEW OF THE DISCLOSURE

Costs of healthcare in the United States continue to increase and are reaching unsustainable levels. Several healthcare industry analysis point to the fact that this is unsustainable, and something must be done to reverse the trend. Many attempts have indeed been made to rein in costs, however intended results always seem to not follow, or when they do, they are not long lasting. Contributing to high costs are inefficiencies related to the exchange, storage, and processing of transactions and other data across non-uniform and/or incompatible systems used by primary parties involved in the medical industry (e.g., healthcare providers, employer groups, third party administrators (TPAs), insurance (stop loss) companies).

Therefore, for all the reasons stated above, and the reasons stated below, there is a need in the art to improve storage, processing, and access to data and transactions related to medical services. It is an object of the disclosure to provide a system for storing, processing, and assessing data related to medical services.

Another object of the disclosure is to provide a system that is interoperable with third party systems.

Yet another object of the disclosure is to provide a system that facilitates transparency, security and verifiability of data.

Another object of the disclosure is to provide a system that improves efficiency in storage and processing of data and transactions.

Yet another object of the disclosure is to provide a system that utilizes a smart card to facilitate identification, authentication, and approvals.

Another object of the disclosure is to provide a system that is strong, robust, durable, and fault tolerant.

Yet another object of the disclosure is to provide a system that can be used in many applications.

Another object of the disclosure is to provide a system that provides unique functionality.

Yet another object of the disclosure is to provide a system that facilitates fast processing of data and transactions.

Another object of the disclosure is to provide a system that is scalable.

Yet another object of the disclosure is to provide a system that is distributed.

Another object of the disclosure is to provide a system that is easy and intuitive to use.

Yet another object of the disclosure is to provide a system that saves time.

Another object of the disclosure is to provide a system that improves a user experience.

These and other objects, features, or advantages of the disclosure will become apparent from the specification, figures and claims.

SUMMARY OF THE DISCLOSURE

Figure 1:
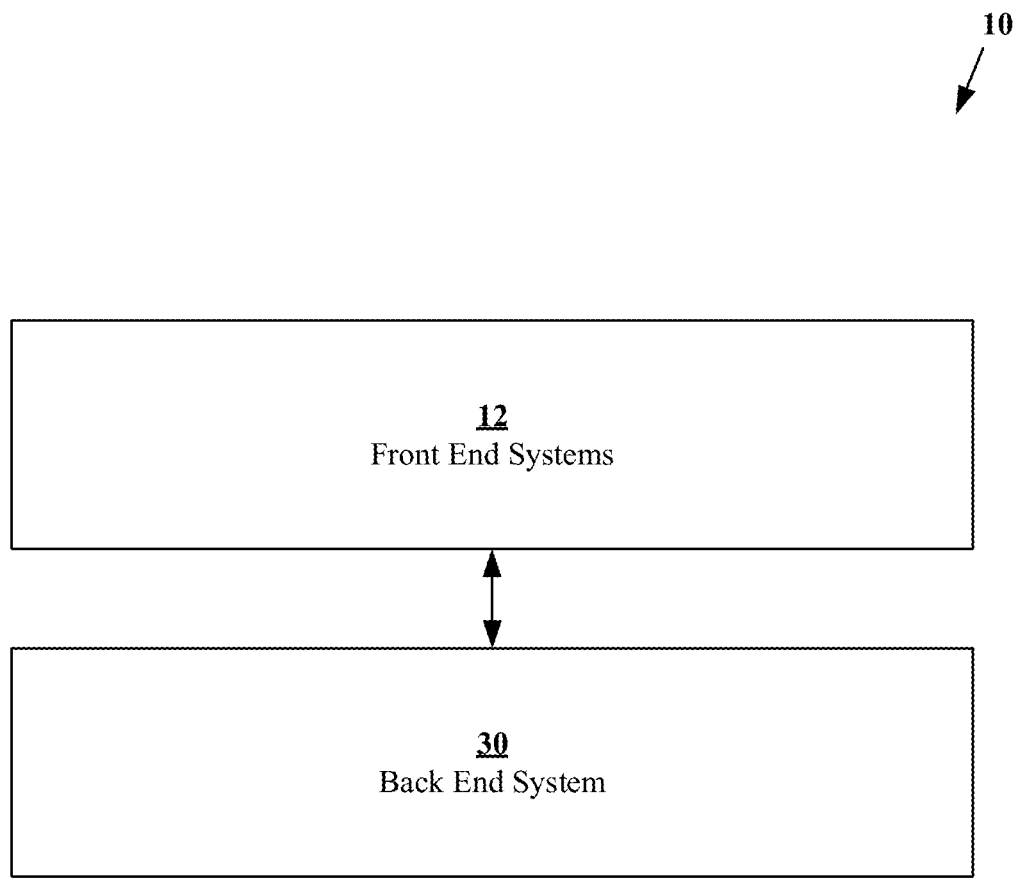
FIG. 1 shows a diagram of a system configured for storing, processing, and/or accessing data, consistent with one or more embodiments.
Figure 2:
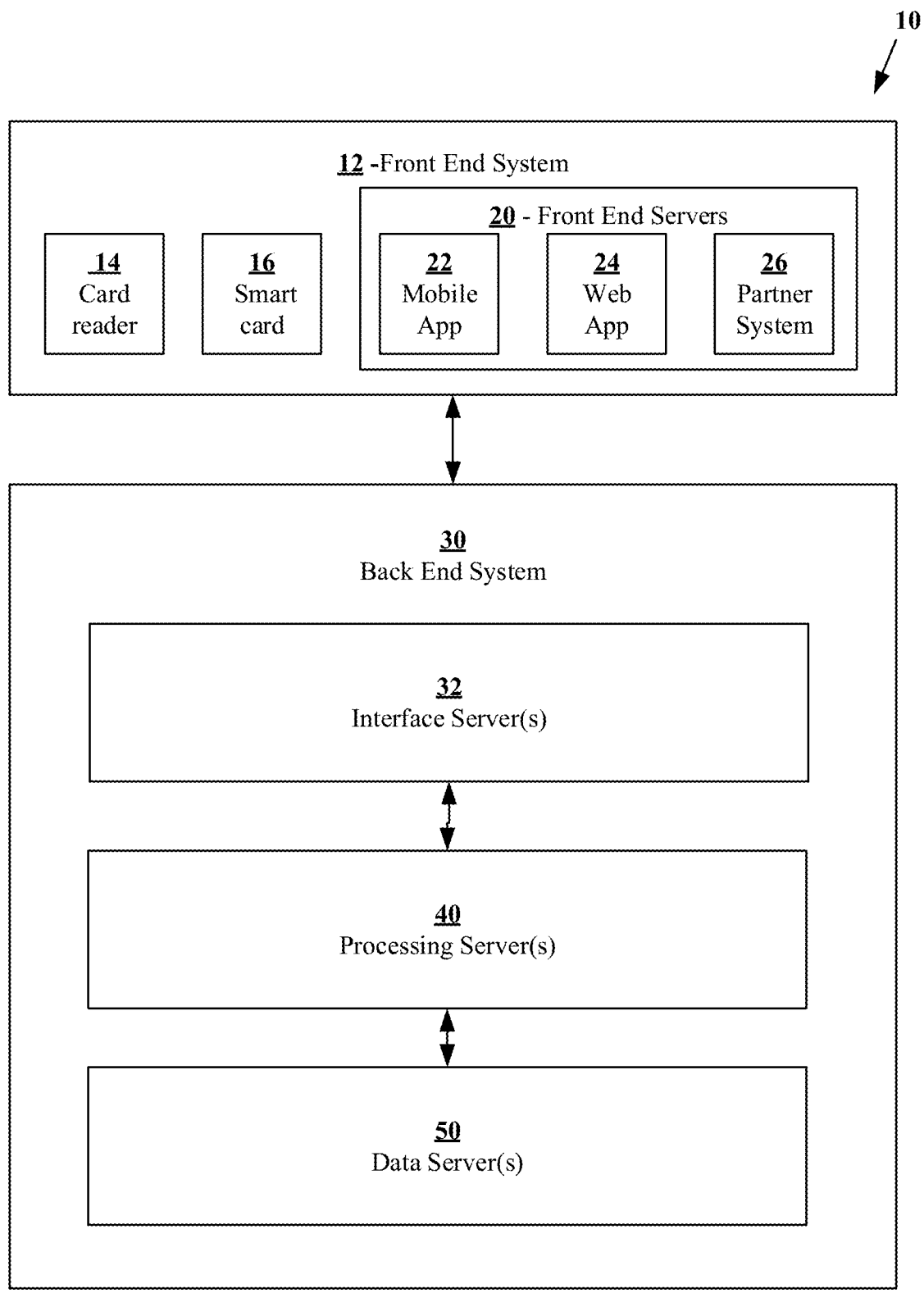
FIG. 2 shows a diagram of the system shown in FIG. 1; the diagram showing example implementations of front end system(s) and back end server(s), consistent with one or more embodiments.
Figure 3:
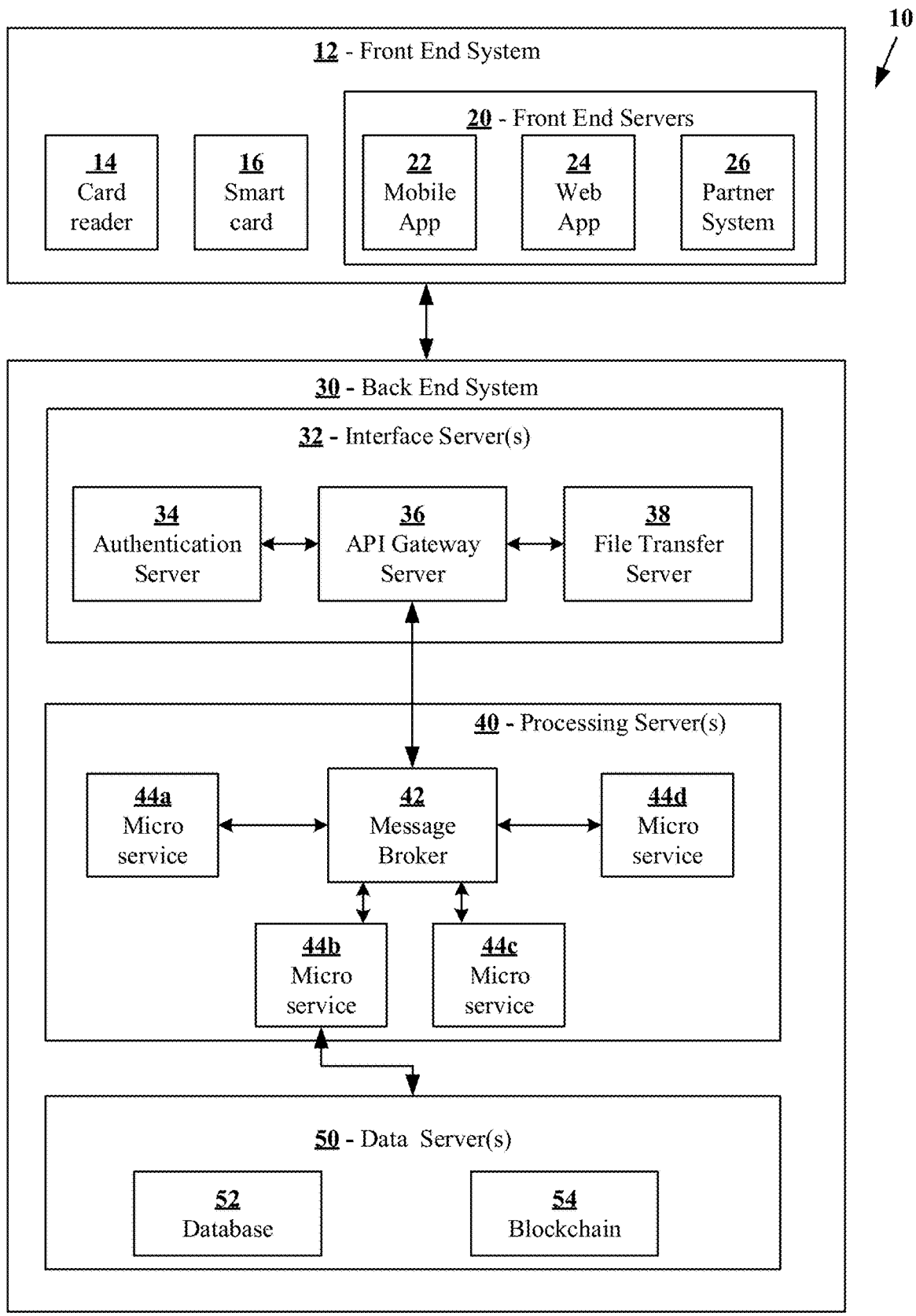
FIG. 3 shows a diagram of the system shown in FIG. 2; the diagram showing example implementations of interface server(s), processing server(s), and data server(s), consistent with one or more embodiments.
Figure 4:
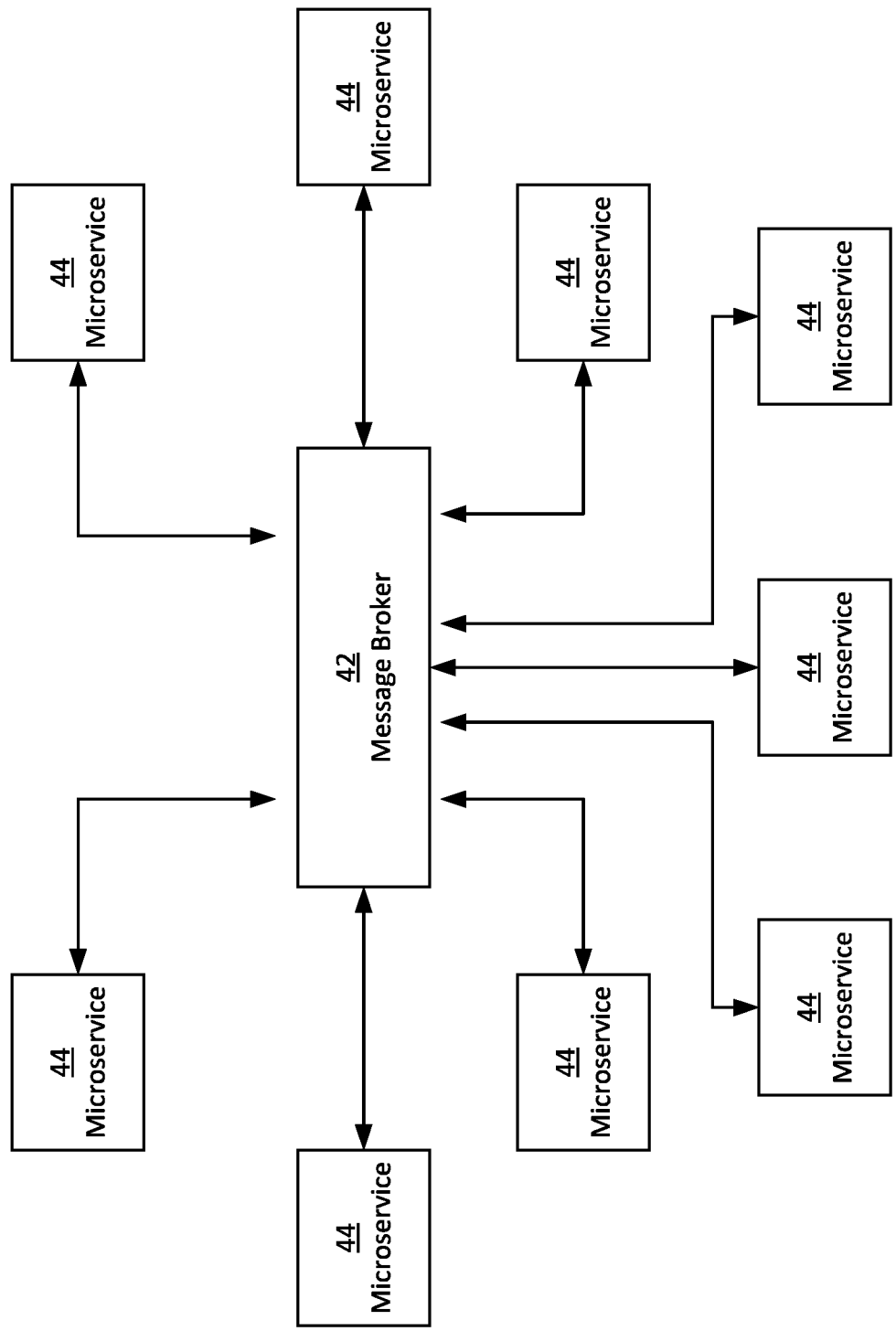
FIG. 4 shows a diagram of a processing server arrangement, consistent with one or more embodiments.

In one or more embodiments, a system is provided for storage, processing, and accessing of data. The system includes a front end system and a back end system communicatively connected to the front end system. The front end system includes one or more front end servers. The back end system includes a first data server. The one or more front end servers are configured to provide one or more user interfaces configured to store, process, and access data in the first data server, in response to user input, by sending messages to the back end system. The back end system includes one or more processing servers communicatively connected to the first data server. The one or more processing servers are configured to process messages received from the front end system by accessing in the first data server to perform one or more operations specified by the messages. The back end system also includes a second data server configured and arranged to maintain a record of changes made to data in the first data server by the one or more processing servers in a blockchain.

In one or more embodiments, the back end system includes one or more interface servers configured to operates as a gateway between the front end system, and the one or more processing servers.

In one or more implementations, the one or more interface servers includes an application program interface (API) server. The API server is configured to: receive the messages from the front end system; attempt to authenticate the received messages; forward ones of the authenticated messages that pass authentication to the one or more processing servers; and discard ones of the authenticated messages that fail authentication. In one or more implementations, the one or more interface servers includes an authentication server to perform the authentication.

In one or more implementations, the one or more interface servers includes a file transfer server configured to receive files from at least one server of the front end system using a file transfer protocol. In response to receiving a file from the front end system, the file transfer server is configured and arranged to: determine a sender of the file; retrieve a file format corresponding to the sender from a memory; and submit the file to the API server as a message in response to determining the file complies with the retrieved file format.

In one or more embodiments, the messages include a plurality of different types of messages. The one or more processing servers are configured and arranged to provide a plurality of micro services, each being is configured to process a subset of the different types of messages. In one or more implementations, the plurality of micro services includes a first micro service configured to process messages requesting changes to health care plan portfolios. In one or more implementations, the plurality of micro services includes a second micro service configured to process messages requesting access to the first data server or the second data server. In one or more implementations, the plurality of micro services includes a third micro service configured to process messages requesting setup of a new group health care plan.

In one or more embodiments, the one or more processing servers includes a message broker. The messages broker includes respective queue for each of the plurality of micro services. The messages broker is configured and arranged to receive the messages from the front end system and place each message in the respective queue of the micro service configured to process the message. The message broker is also configured to forward the next message in a queue to the respective micro service, in response to the micro service becoming available. In one or more embodiments, the micro services are configured to send messages to other micro services by sending the messages to the message broker.

In one of more embodiments, the front end system includes one or more card readers. The back end system is configured to authenticate the users with smart cards using the one or more card readers.

DETAILED DESCRIPTION OF THE DISCLOSURE

In the following detailed description of the embodiments, reference is made to the accompanying drawings which form a part hereof, and in which is shown by way of illustration specific embodiments in which the disclosure may be practiced. The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure. It will be understood by those skilled in the art that various changes in form and details may be made without departing from the principles and scope of the invention. It is intended to cover various modifications and similar arrangements and procedures, and the scope of the appended claims therefore should be accorded the broadest interpretation so as to encompass all such modifications and similar arrangements and procedures. For instance, although aspects and features may be illustrated in or described with reference to certain figures or embodiments, it will be appreciated that features from one figure or embodiment may be combined with features of another figure or embodiment even though the combination is not explicitly shown or explicitly described as a combination. In the depicted embodiments, like reference numbers refer to like elements throughout the various drawings.

It should be understood that any advantages and/or improvements discussed herein may not be provided by various disclosed embodiments, or implementations thereof. The contemplated embodiments are not so limited and should not be interpreted as being restricted to embodiments which provide such advantages or improvements. Similarly, it should be understood that various embodiments may not address all or any objects of the disclosure or objects of the invention that may be described herein. The contemplated embodiments are not so limited and should not be interpreted as being restricted to embodiments which address such objects of the disclosure or invention. Furthermore, although some disclosed embodiments may be described relative to specific materials, embodiments are not limited to the specific materials or apparatuses but only to their specific characteristics and capabilities and other materials and apparatuses can be substituted as is well understood by those skilled in the art in view of the present disclosure.

It is to be understood that the terms such as "left, right, top, bottom, front, back, side, height, length, width, upper, lower, interior, exterior, inner, outer, and the like as may be used herein, merely describe points of reference and do not limit the present invention to any particular orientation or configuration.

As used herein, the term "or" includes one or more of the associated listed items, such that "A or B" means "either A or B". As used herein, the term "and" includes all combinations of one or more of the associated listed items, such that "A and B" means "A as well as B." The use of "and/or" includes all combinations of one or more of the associated listed items, such that "A and/or B" includes "A but not B," "B but not A," and "A as well as B," unless it is clearly indicated that only a single item, subgroup of items, or all items are present. The use of "etc." is defined as "et cetera" and indicates the inclusion of all other elements belonging to the same group of the preceding items, in any "and/or" combination(s).

As used herein, the singular forms "a," "an," and "the" are intended to include both the singular and plural forms, unless the language explicitly indicates otherwise. Indefinite articles like "a" and "an" introduce or refer to any modified term, both previously-introduced and not, while definite articles like "the" refer to a same previously-introduced term; as such, it is understood that "a" or "an" modify items that are permitted to be previously-introduced or new, while definite articles modify an item that is the same as immediately previously presented. It will be further understood that the terms "comprises," "comprising," "includes," and/or "including," when used herein, specify the presence of stated features, characteristics, steps, operations, elements, and/or components, but do not themselves preclude the presence or addition of one or more other features, characteristics, steps, operations, elements, components, and/or groups thereof.

It will be understood that when an element is referred to as being "connected," "coupled," "mated," "attached," "fixed," etc. to another element, it can be directly connected to the other element, and/or intervening elements may be present. In contrast, when an element is referred to as being "directly connected," "directly coupled," "directly engaged" etc. to another element, there are no intervening elements present. Other words used to describe the relationship between elements should be interpreted in a like fashion (e.g., "between" versus "directly between," "adjacent" versus "directly adjacent," "engaged" versus "directly engaged," etc.). Similarly, a term such as "operatively", such as when used as "operatively connected" or "operatively engaged" is to be interpreted as connected or engaged, respectively, in any manner that facilitates operation, which may include being directly connected, indirectly connected, electronically connected, wirelessly connected or connected by any other manner, method or means that facilitates desired operation. Similarly, a term such as "communicatively connected" includes all variations of information exchange and routing between two electronic devices, including intermediary devices, networks, etc., connected wirelessly or not. Similarly, "connected" or other similar language particularly for electronic components is intended to mean connected by any means, either directly or indirectly, wired and/or wirelessly, such that electricity and/or information may be transmitted between the components.

It will be understood that, although the ordinal terms "first," "second," etc. may be used herein to describe various elements, these elements should not be limited to any order by these terms unless specifically stated as such. These terms are used only to distinguish one element from another; where there are "second" or higher ordinals, there merely must be a number of elements, without necessarily any difference or other relationship. For example, a first element could be termed a second element, and, similarly, a second element could be termed a first element, without departing from the scope of example embodiments or methods.

Similarly, the structures and operations discussed herein may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, to provide looping or other series of operations aside from single operations described below. It should be presumed that any embodiment or method having features and functionality described below, in any workable combination, falls within the scope of example embodiments.

As used herein, various disclosed embodiments may be primarily described in the context of the health care and medical related services. However, the embodiments are not so limited. It is appreciated that the embodiments may be adapted for use in other applications which may be improved by the disclosed structures, arrangements and/or methods. The system is merely shown and described as being used in in the context of health care and medical related services for ease of description and as one of countless examples.

System 10:

With reference to the figures, a networked computing system 10 (or simply system 10) is presented. The system 10 is formed of any suitable design, arrangement, and circuitry and is configured to facilitate storing, processing, and accessing data related to medical services. In one or more arrangements, as shown in FIG. 1 for example, the system 10 includes a front end system 12 and one or more back end system 30 among other components. Front end system 12 and back end system 30 are communicatively connected over one or more data networks.

Front End System 12:

In one or more arrangements, system 10 includes a front end system 12. Front end system 12 is formed of any suitable design, arrangement, and circuitry and are configured to facilitate storage, processing, or access to data in back end system 30 by end users. In the arrangement shown, front end system 12 include a number of front end servers 20, a card reader 14, and a smart card 16, among other components.

Card Reader 14 and Smart Card 16:

Card reader 14 and smart card 16 are formed of any suitable design, arrangement, and circuitry and are configured to facilitate exchanges of data between the smart card 16 and the card reader 14 and facilitate authentication of a card holder. In some various arrangements, for example, smart card 16 and the card reader 14 may be configured to communicate via direct electrical connection (e.g., when smart card 16 is inserted into card reader 14), wirelessly (e.g., using RFID), and/or any other communication method.

In one or more arrangements, smart card 16 includes a processing chip and a memory storing a secret key that may be used to authenticate the card holder (e.g., a symmetric or asymmetric key) with an authentication server. As an illustrative example, via the card reader 14, an authenticating entity may provide a challenge number to the smart card 16. The processing chip performs a mathematical function (e.g., encryption, decryption, etc.) that uses the challenge number and secret key as input. After computing, the smart card 16 communicates the result back to the authenticating entity. If the result matches the number expected by the authentication service, the smart card 16 is authenticated. However, embodiments are not so limited. Rather, as described in more detail with reference to authentication server 34, some various embodiments may utilize various processes and/or technologies to perform authentication using a smart card 16.

Front End Servers 20:

Front end servers 20 are formed of any suitable design, arrangement, and circuitry and are configured to provide an interface for end-users to communicate with back end system 30 to store, process, or access data stored therein. In the arrangement shown, as one example, front end servers 20 includes mobile applications 22, web servers providing web apps 24, and/or partner computer systems 26 configured to communicate with back end system 30 over one or more data networks. In one or more arrangements, one or more front end servers 20 are configured to interface with card reader 14 to authenticate or obtaining other information from smart card 16. For example, a front end server 20 may be configured to authenticate a user and/or obtain user information to facilitate faster login and interaction with a user portal, while reducing user errors (e.g., due to mistyping). As another example, a front end server 20 may be configured to provide an electronic payment system that uses the smart card 16 as method of payment. For instance, in one or more arrangements, system 10 may be configured to debit from a healthcare savings account, bank account, or other payment system linked to the smart card 16 by a health plan member, thereby permitting the member to use the smart card 16 for payment of a copay.

In Operation:

As an illustrative example, the use of smart card 16 and card reader 14 in connection with front end servers 20 is thought to be particularly useful in the health care context, for example, to facilitate identification and authentication of health plan member seeking medical services and facilitate permitted access and exchanges of data related to the member and/or medical services.

Continuing with the example in the health care context, in one or more arrangements, the front end servers 20 may be configure to provide respective user interface (e.g., web portal, mobile apps, and/or computer program), to facilitate storage of, processing of, and/or access to data in back end system 30, for various groups of users including, for example: health care consumers (e.g., employers, employees/health plan members, and/or health plan member dependents), health care providers (e.g., hospitals, clinics, and/or physicians), and payers (e.g., insurance companies, third-party administrators, and/or stop loss carriers).

User interface for different groups of users may provide access to different data resources processes and/or functions provided by back end system 30. As an illustrative example, a front end server 20 may be configured to provide a user interface for a health care provider. In this example, the user interface may permit users to engage with the back end system 30 to perform a number of actions including but not limited to, for example, authenticating and verifying eligibility of health plan members; importing health plan information into provider systems; submitting pre-authorization requests for procedures; editing provider profile information, retrieving and viewing medical/drug history of a health plan member (if authorized by the health plan member); and/or storing medical records.

As another illustrative, a front end server 20 may be configured to provide a user interface for health plan members. In this example, the user interface may permit members to engage with the back end system 30 to perform a number of actions including but not limited to, managing profile and dependent information, configuring multi-factor authentication, accessing of medical/drug history records, granting third parties access to medical/drug history records, managing prescriptions, and/or managing payment services.

As yet another illustrative, a front end server 20 may be configured to provide a user interface for a third party administrator. In this example, the user interface may permit third party administrator employees to engage with the back end system 30 to perform a number of actions including but not limited to, onboarding groups for new health plans, collecting claims data, storing data, updating group data, updating employee data, and/or updating dependent data.

Back End System 30:

Turning now to back end system 30, in one or more arrangements, system 10 includes one or more back end system 30. Back end system 30 is formed of any suitable design, arrangement, and circuitry and are configured to store, process and access to data, in response to requests from users via front end system 12, and is further configured to authenticate and restrict user's ability to store, process, and/or access data based on permissions allocated for the user. In the arrangement show, as one example, back end system 30 includes one or more interface servers 32, one or more processing servers 40, and one or more data servers 50, among other components. Interface servers 32, processing servers 40, and data servers 50 are communicatively connected over one or more data networks and/or data buses.

Interface Server(s) 32:

Interface server(s) 32 are formed of any suitable design, arrangement, and circuitry and is configured to operate as an interface for front end system 12 to access resources and/or functionality provided by back end system 30. In one arrangement shown, as one example, interface server(s) 32 include an authentication server 34, an API gateway server 36, and a file transfer server 38 communicatively connected over one or more data networks and/or data buses.

Authentication Server 34:

Authentication server 34 is formed of any suitable design, arrangement, and circuitry and is configured to authenticate users of front end system 12. In various embodiments, authentication server 34 is configured to authenticate users using one or more authentication techniques and/or protocols including but not limited to, for example: Password Authentication Protocols, Challenge-Handshake Authentication Protocol, Extensible Authentication Protocol, Terminal Access Controller Access-Control System protocols, Remote Authentication Dial-In User Service, Diameter, Kerberos, Authentication and Key Agreement, CAVE-based authentication, CRAM-MD5, Digest, Host Identity Protocol, LAN Manager, NT LAN Manager, Open ID protocol, Password-authenticated key agreement protocols, Protocol for Carrying Authentication for Network Access, Secure Remote Password protocol, RFID-Authentication Protocols, Woo Lam 92 (protocol), Security Assertion Markup Language, and/or any other known authentication protocol.

API Gateway Server 36:

API gateway server 36 is formed of any suitable design, arrangement, and circuitry and is configured to operate as an interface for communication of messages between interface servers 32 and processing servers 40. In one or more embodiments, messages may include various data including but not limited to, for example, requests for data from data servers 50, request to store or modify data in data servers 50, and/or requests for performance of one or more functions provided by back end system 30 (e.g., functions performed by micro services 44).

Figure 5:
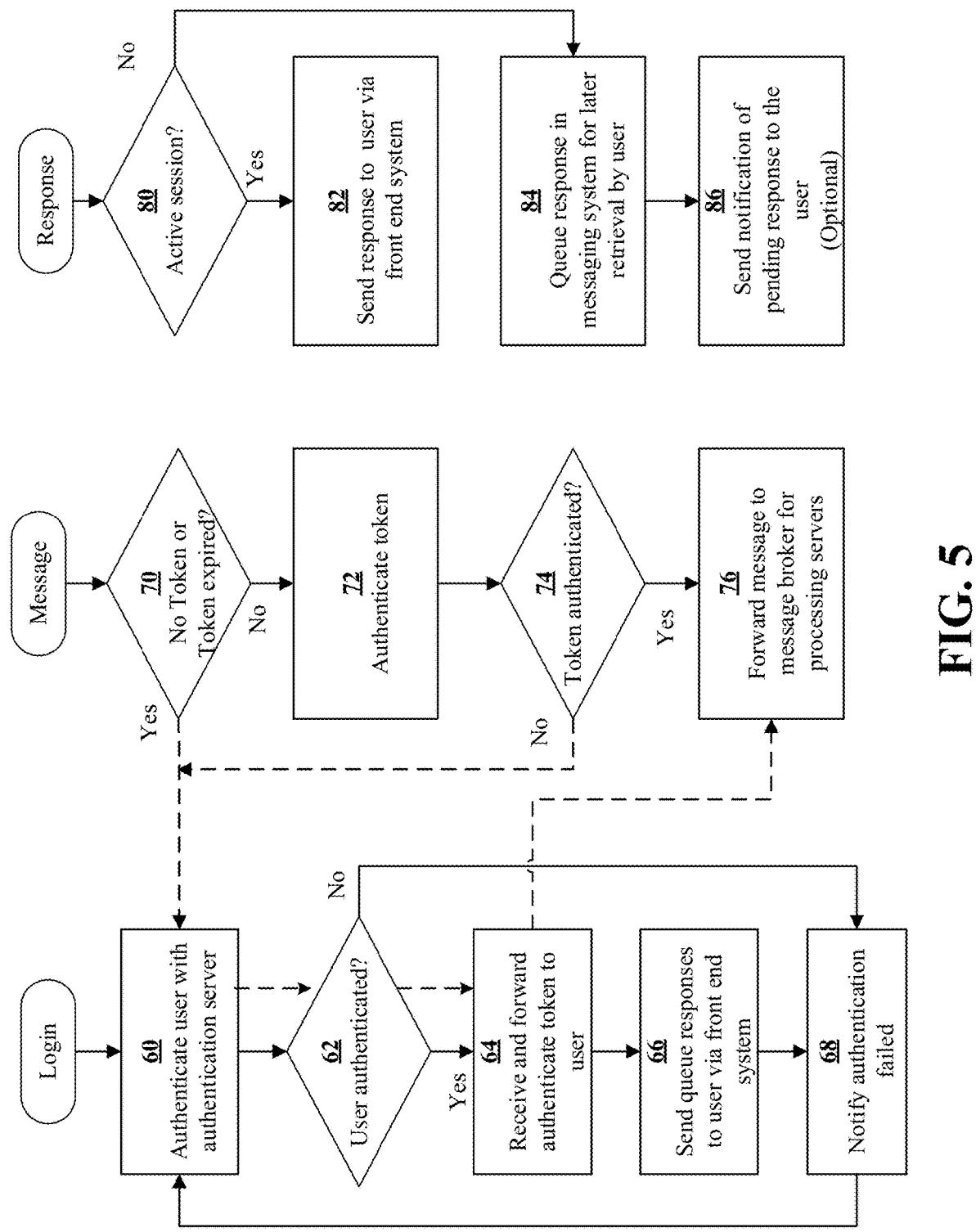
FIG. 5 shows a diagram of an example processes performed by API gateway server, consistent with one or more embodiments.
Figure 6:
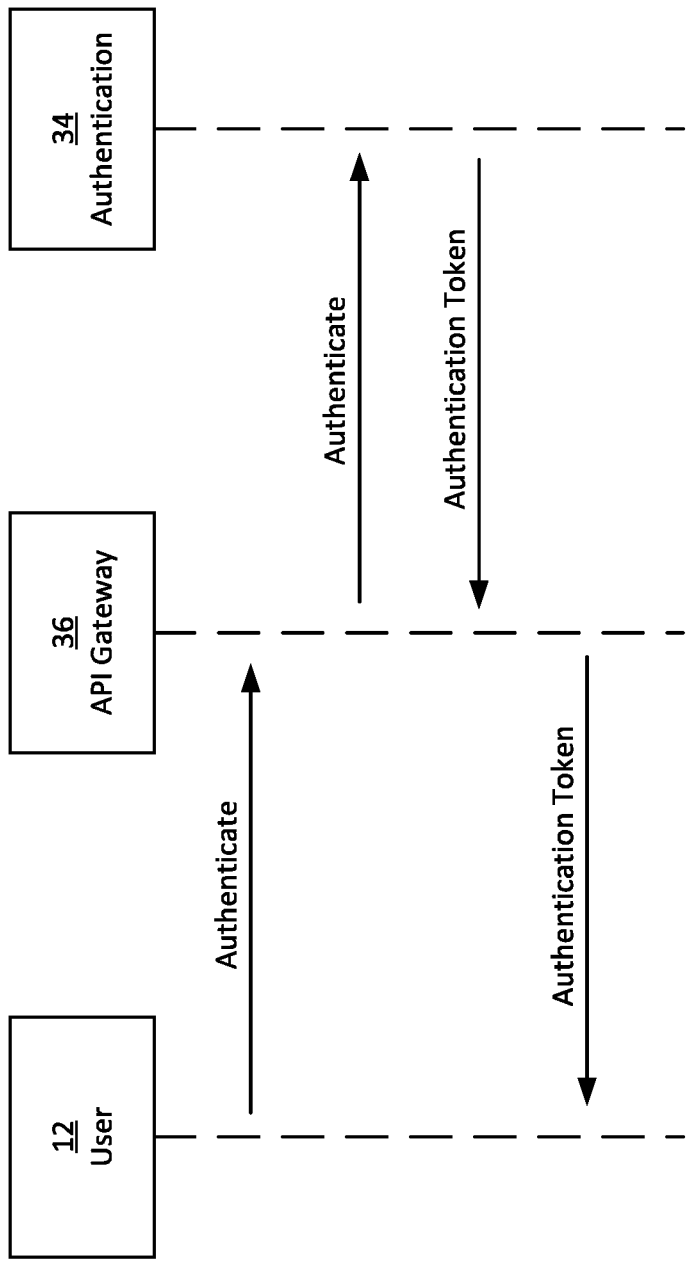
FIG. 6 shows a diagram of an example message flow for initial authentication of a user, consistent with one or more embodiments.
Figure 7:
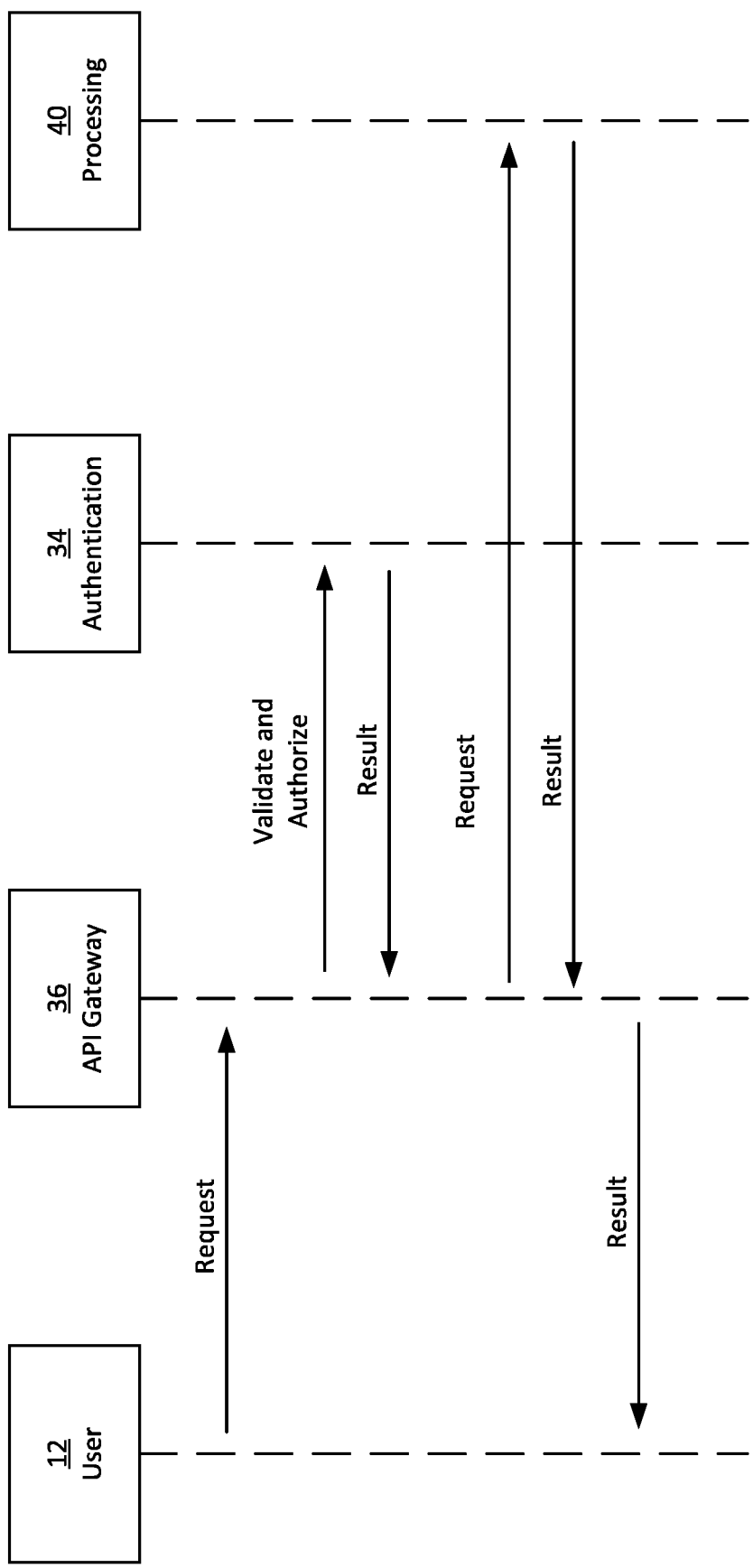
FIG. 7 shows a diagram of an example message flow for handling of messages by the API gateway server, consistent with one or more embodiments.

FIG. 5 shows a diagram of example processes performed by API gateway server, consistent with one or more embodiments. In response to a user attempting login to a front end system 12, API gateway server 36 authenticates the user with authentication server 34. If user is authenticated at decision block 62, an authentication token is received and forwarded to the user at block 64. Otherwise, the user is notified that authentication failed at block 68 and authentication is reattempted at block 60. The process continues in this manner until user is authenticated or user gives up. In some implementations, a user may be locked out of the system if authentication fails a number of times.

After the authentication token is forwarded to the user at block 64, any messages waiting for the user are sent to the user at block 66 via front end system 12. In this example, after authentication token is issued, the authentication token is used to authenticate messages subsequent submitted to API gateway server 36 by user. For ease of explanation, the example processes are described with reference to authentication tokens that remain valid for remainder of the user session. However, embodiments are not so limited. Rather, in some implementations, authentication tokens may remain valid for shorter or longer periods of time or even indefinitely.

In response to receiving a message from front end system 12, API gateway server 36 performs the process starting at decision block 70. If the received message includes an active token at decision block 70, the API gateway server 36 authenticates the authentication token with authentication server 34 at block 72. If token is successfully authenticated at decision block 76, API gateway server 36 forwards the message to message broker 42 of processing servers 40 at block 76.

If the received message does not include an authentication token or if the authentication token is expired at decision block 70 or if authentication of the token failed at decision block 74, the process proceeds to block 60 to authenticate or reauthenticate the sender or the message as previously described with reference to blocks 60,62,64, 66, and 68. If authentication is successful, the process proceeds to block 76 where API gateway server 36 forwards the message to message broker 42 of processing servers 40 for processing. Otherwise, the message is discarded.

As will be described in more detail with reference to processing servers 40, processing servers 40 may processes messages received from API gateway server 36 in a stateless asynchronized manner, where response time is not guaranteed. Accordingly, it is possible that a user session may end before the message is processed and a response (e.g., requested data, report, or confirmation of performed action) is provided back to API gateway server 36.

In response to receiving a response from processing servers 40, API gateway server 36 performs the process starting at decision block 80. If a session for the sender that submitted the original message is active at decision block 80, API gateway server 36 sends the response to the user via front end system 12. If the user does not have an active session at decision block 80, the response is queued in a messaging system at block 84 for later retrieval by the user. In some implementations, API gateway server may also send a notification (e.g., SMS, email, and/or push notification) that response is pending to the user.

File Transfer Server 38:

File transfer server 38 is formed of any suitable design, arrangement, and circuitry and is configured to receive data files from front end servers 20 for processing by back end system 30. File transfer server 38 may be used, for example, to enable partner systems 26 that are not configured to communicate directly with API gateway server 36 to submit data files for processing by back end system 30. File transfer server 38 may be configured to receive files using one or more file transfer protocol including but not limited to, for example, SFTP, FTPS, ASS2, HTTPS, MFT, and/or any other known file transfer protocol.

Figure 8:
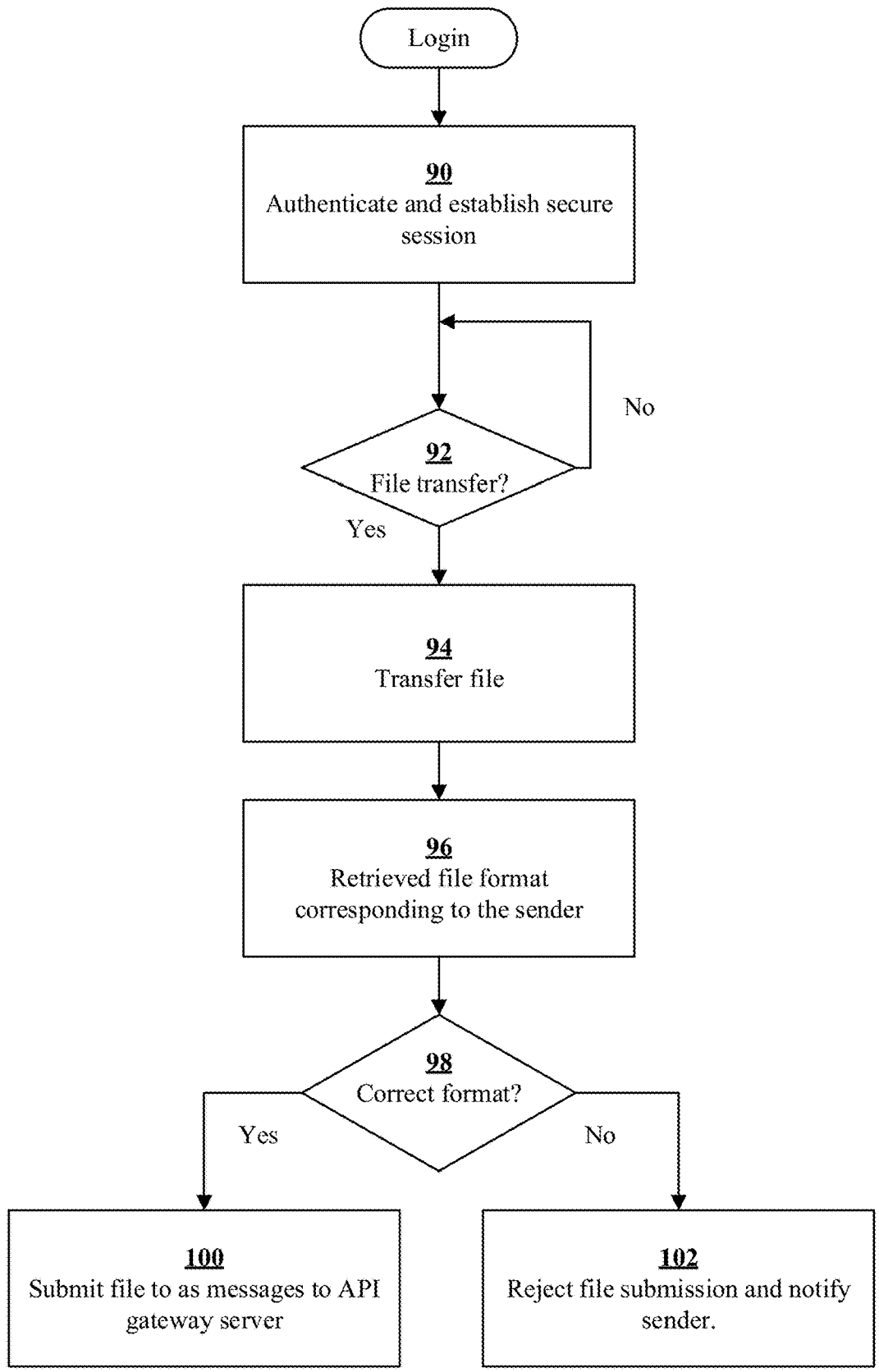
FIG. 8 shows a diagram of an example process performed by file transfer server, consistent with one or more embodiments.

FIG. 8 shows a diagram of an example process performed by file transfer server 38, consistent with one or more embodiments. In response to login request to file transfer server 38 (e.g., by a partner system 26), the user/system is authenticated, and a secure session is established at block 90. In this example, the file transfer server 38 waits at decision block 92 until a file transfer is requested. Once a transfer is requested, the file is transferred to the file transfer server 38 at block 94.

As previously noted, file transfer server 38 may be used in some situations to enable partner systems 26 that are not configured to communicate API gateway server 36 to submit files. Such partner systems may be configured to submit data files in their own unique file formats. To facilitate processing of partner format files, in one or more embodiments, back end system 30 is configured to store and use one or more agreed to formats previously provided by the partners. In this example process, file transfer server 38 is configured to check received files to ensure the files are in a format that can be processed by back end system 30. At block 96, file transfer server 38 retrieves a file format corresponding to the logged in sender (e.g., from a memory). If the file does not follow the retrieved format for the sender, at decision block 98, file transfer server 38 rejects the file submission and notifies the sender at block 102. If the file complies with the retrieved format, file transfer server 38 submits the file as a message to the API gateway server.

Processing Server(s) 40:

Processing server(s) 40 is formed of any suitable design, arrangement, and circuitry and is configured to process files and/or messages for the back end server to facilitate user access to resources and/or functionality provided by back end system 30. In an arrangement shown, as one example, processing server(s) 40 include a message broker 42 and a plurality of micro services 44.

Message Broker 42:

Message broker 42 is formed of any suitable design, arrangement, and circuitry and is configured to facilitate routing and communicating of messages and/or files to micro services 44 for processing. In an arrangement shown, as one example, message broker 42 is communicatively connected to micro services 44 and to API gateway server 36 via one or more data networks and/or data busses. In this example arrangement, message broker 42 is configured to operate as the primary channel for communicating messages/files to each micro service 44 for processing.

Figure 9:
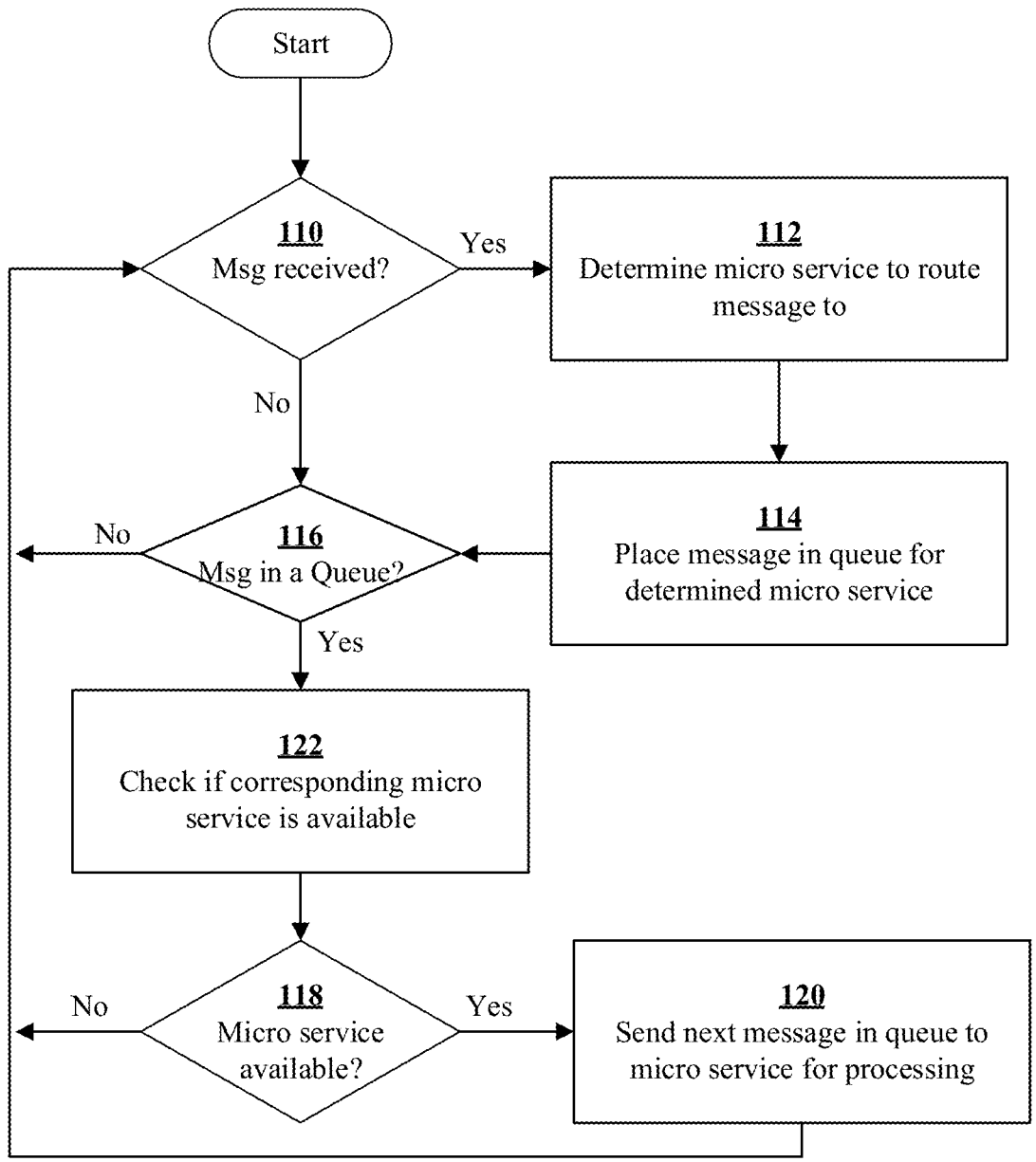
FIG. 9 shows a diagram of an example process performed by message broker, consistent with one or more embodiments.

In various embodiments, message broker 42 may perform routing and communicating messages using any suitable set of processes or tasks. FIG. 9 shows an example process that may be performed by message broker 42 for routing and communicating messages in one or more embodiments. In this example, process starts at decision block 110. If a message is received at decision block 110, message broker 42 determines the appropriate micro service 44 to route the message to at block 112. At block 114, message broker 42 places the message in a respective queue within message broker 42 for the determined micro service 44 and proceeds to decision block 116. At decision block 116, the message broker 42 checks messages queues. For any queue having a message pending, message broker 42 checks at block 122 to see if the corresponding micro service 44 is available. If the micro service 44 is available at decision block 118, message broker 42 sends the next message in the queue to the micro service 44 for processing at block 120. If the corresponding micro service(s) 44 for waiting messages is not available at decision block 118, or if no messages are waiting in queue at decision block 116, the process returns to decision block 110 and the example process is repeated.

Micro Services 44:

Micro Services 44 are formed of any suitable design, arrangement, and circuitry and are configured to process messages and/or data files to provide various resources and/or functionality to users. In various embodiments, processing servers 40 may include any number of micro services 44. In various embodiments, micro services 44 may also be configured to perform any number of different functions. In performing various functions, micro services 44 may perform functions autonomously and/or may generate messages to other micro services 44 to request performance of other functions.

In Operation:

For ease of explanation, and continuing with the example in the healthcare context, example arrangements are primarily discussed with reference to processing servers 40 having an arrangement of four example micro services 44: a portfolio management micro service 44a, a data access micro service 44b, a business management micro service 44c, and a file processing micro service 44d.

In this example arrangement, in one or more embodiments, portfolio management micro service 44a is configured to perform changes to health plan portfolio data. Portfolio data may include but is not limited to, for example, information, preferences, and/or transaction history for the employer, employee/member, and/or member dependents.

In this example arrangement, data access micro service 44b is communicatively connected to message broker 42 and data server 50. Data access micro service 44b is configured to perform operations to access data server 50 in response to requests received from interface servers 32 or other micro services 44.

In this example arrangement, business management micro service 44c is configured to perform a number of business related administrative tasks including but not limited to, for example, smart card manufacturing processes, notification and statement mailing, pre-authorization (case management) processes, health plan sales and quoting processes, etc.

In this example arrangement, file processing micro service 44d is configured to process files received and submitted by file transfer server 38. As an illustrative example, a third party administrator may submit a file for the sale of a new employer health plan. In processing the file, file processing micro service 44d may send one or more messages to portfolio management micro service 44a, via messages broker 42, to request creation of portfolio entries for the employer, employee/member, dependents, etc. File processing micro service 44d may also send one or more messages to business management micro service 44c, via messages broker 42, for example, to request generation of smart cards for new employee members and mailing of new member documents. In some scenarios, file processing micro service 44d may also send one or more messages to data access management micro service 44b, for example, to request information specified in the processed file. In processing the requests from file processing micro service 44d, portfolio management micro service 44a and business management micro service 44c may also generate and submits messages for other micro services 44 to the messages broker 42. For instance, portfolio management micro service 44a and business management micro service 44c may send messages to data access micro service 44b, via message broker 42, to read data from and/or write data to data servers 50.

While various components of system 10 may be primarily illustrated and described as separate components, embodiments are not so limited. Rather, it is understood that separate components may be combined and implemented together as a single component. Conversely, it is understood that a single component may be split and implemented by separate communicatively connected components. As an illustrative example, micro services 44a, 44b, 44c, and 44d may be implemented by respective computer servers or circuits, by respective computing resources (e.g., processors/cores and memory) in a shared computer server, and/or by respective processes/threads operating on shared computing resources.

Additionally or alternatively, in one or more embodiments, one or more micro services 44 may be implemented by a separate platform system. For example, business management micro service 44c may use a third party platform to one or more business related processes (e.g., smart card manufacturing, notification and statement mailing, pre-authorization (case management) processes, health plan sales and quoting processes.

Data Server(s) 50:

Data server(s) 50 are formed of any suitable design, arrangement, and circuitry and are configured to store data. In an arrangement shown, as one example, data server includes a database server 54 and a blockchain server 54.

In this example arrangement, database server 54 is configured to store all data for system 10. Continuing with the illustrative example in the healthcare context, data for the system 10 may include but is not limited to, for example, group and member data, medical history, billing transactions and records, pre-authorization requests, insurer information, provider information, service locations, and/or related other health care related records.

In this example arrangement, blockchain server 54 is configured to record a history of transactions and/or events in the system 10 a blockchain. Block chains utilize a self-referencing data structure to store data as a series of blocks. Generally, each block includes contains a cryptographic reference (e.g., a hash) of the previous block, a timestamp, and a set of data. Once recorded, the data in any given block cannot be altered retroactively without alteration of all subsequent blocks. This arrangement makes blockchains extremely resistant to tampering or modification of data, Blockchains enable the traversal backwards in time across all previously, recorded blocks to prove the validity of the data written therein. In the healthcare context, storing the history of transactions and/or events in a block chain can be used to increase transparency for plan members, providers, and payers. It is anticipated that increased transparency will improve the quality of care, improve efficiency, and reduce health care costs.

In some arrangements, block chain server 54 is a stand-alone block chain server. Alternatively, in some arrangements, block chain server 54 may be one node in a block chain network having redundant copies of the block chain distributed and synchronized across a plurality of nodes.

Figure 10:
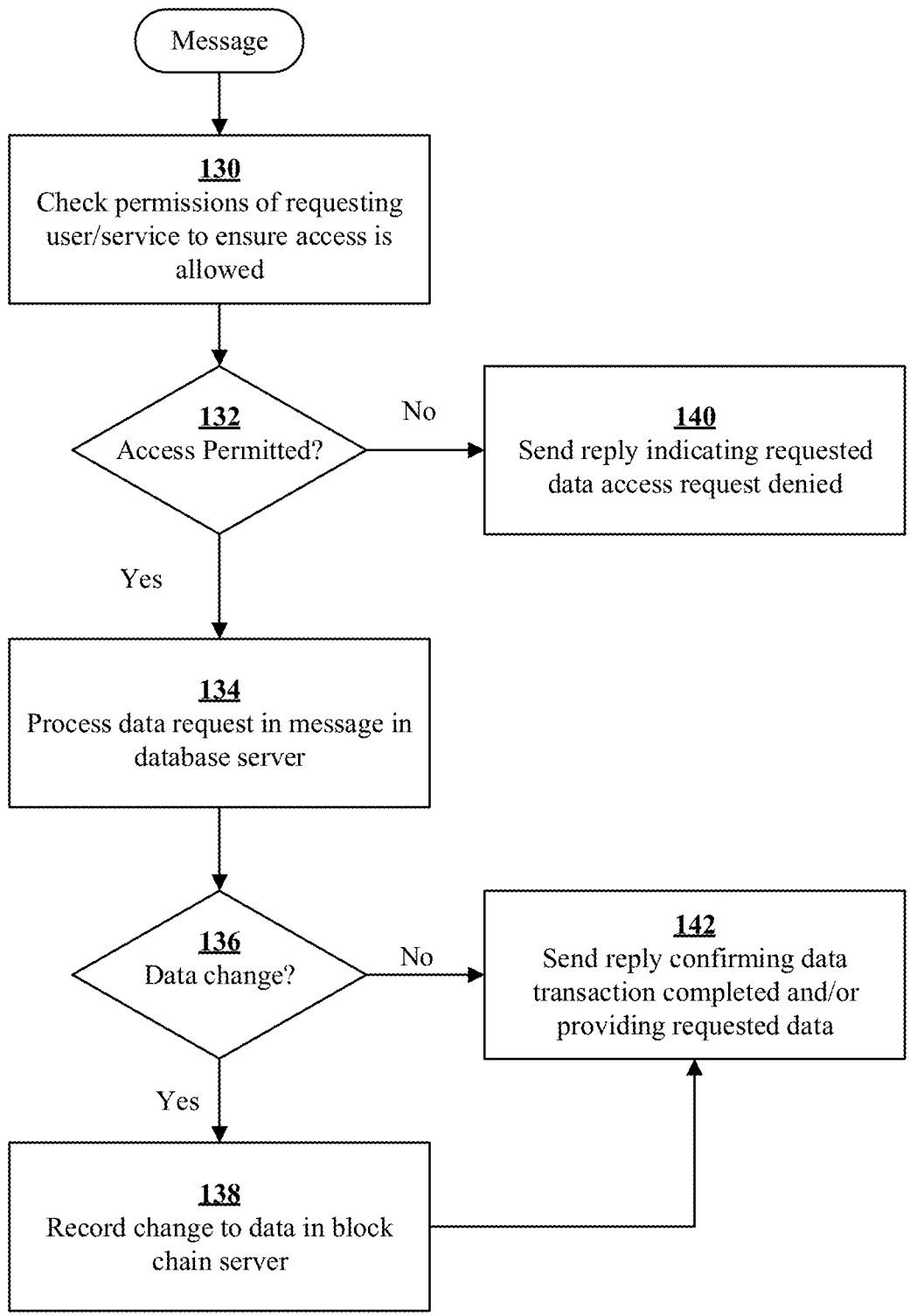
FIG. 10 shows a diagram of an example process performed by data servers, consistent with one or more embodiments.
Figure 11:
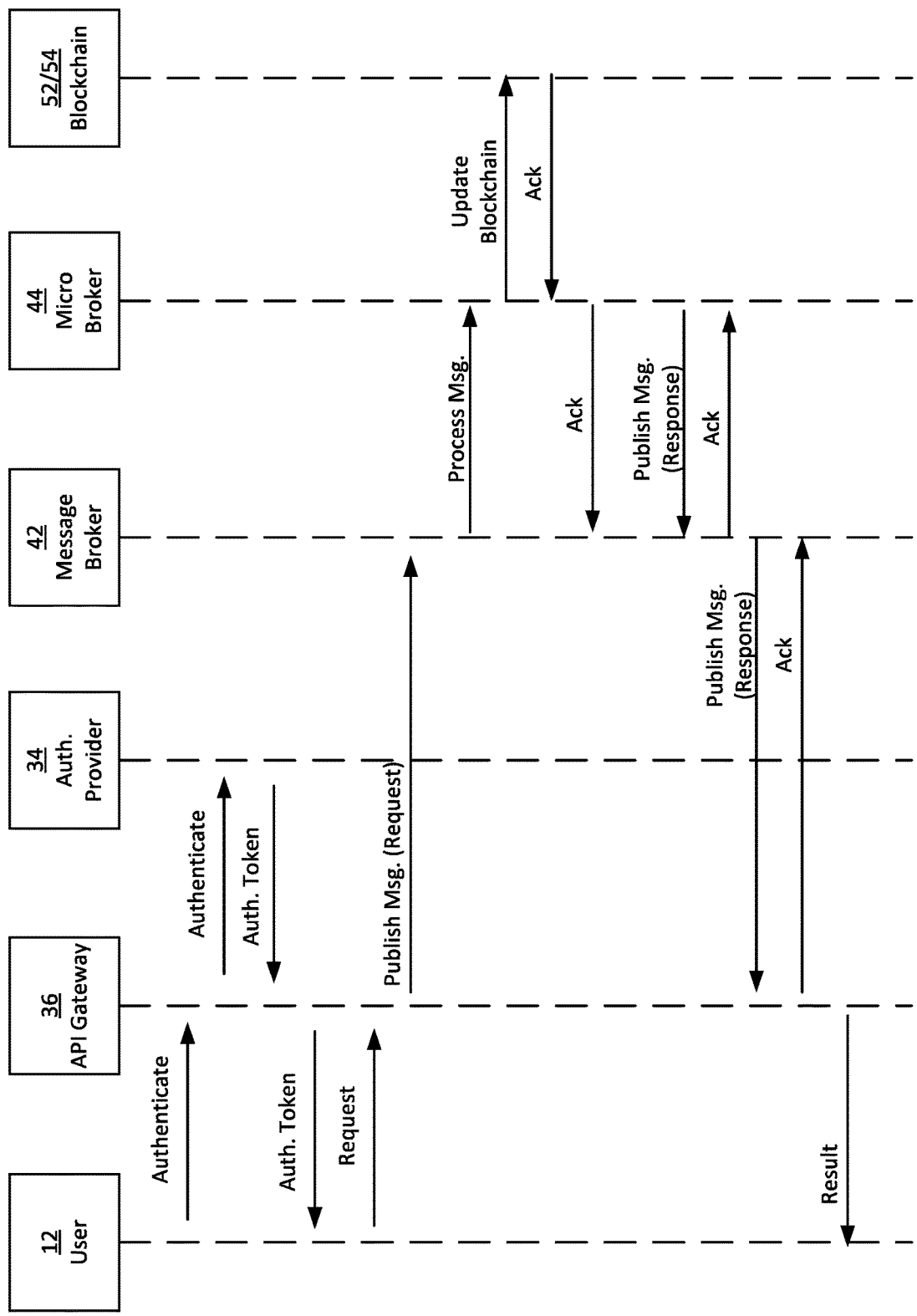
FIG. 11 shows a diagram of an example message flow, consistent with one or more embodiments.

FIG. 10 shows a diagram of an example process performed by data servers 50, consistent with one or more embodiments. In this example, in response to receiving a message, data servers 50 checks permissions of the requesting user/service to ensure that the requested access is allowed. For example, in one or more implementations, permissions of the requesting user/service may be determined by examining an authentication token that is included with the message. For instance, in one or more implementations, the authentication token may indicate a permission level or an identifier from which permitted accesses may be determined (e.g., by looking up data resources to be accessed in a permissions table stored in a memory). In some various implementations, permission for access to different data resources may be specified for groups or categories of users (e.g., health care providers, third party administrators, etc.), for individual users, for categories of data resources, and/or for individual data resources.

If it is determined that the requested data access is not permitted, at decision block 132, data servers 50 send a reply at block 140 indicating that the requested data access request is denied. Otherwise, database server 52 processes the data access request, indicated in the message, in database server 52.

In this example process, data servers 50 are configured to record data transactions in a blockchain only if the transaction changes data. Additionally or alternatively, in some embodiments, data servers 50 are configured to record data transactions in the blockchain that do not change data in database server 52. Recording data accesses that do not change data may be useful, for example, to ensure compliance with the Health Insurance Portability and Accountability Act. If the processed data access request changes data in database server 52, decision block 136 directs the process to block 138, where blockchain server 54 records the data change in a blockchain. If the blockchain is a distributed blockchain, other nodes in the blockchain network are also updated at block 138.

After updating the blockchain at block 138, or if the data access transaction did not change the data, the process proceeds to block 142, where data servers 50 send a reply confirming that the data transaction indicated in the messages was completed and/or providing the requested data.

In Operation:

To facilitate understanding of the interoperation and communication between various components of system 10, some illustrative examples are provided that describe messages flow and operations performed in response to a user request.

Continuing with the example in the health care context, a health plan may be activated for a new member by a third party administrator submitting an eligibility file to system 10. In this example, the eligibility file may be submitted to file transfer server 38 by a front end server 26 of the third party administrator. File transfer server 38 may authenticate the system, receive the file, review file for format requirements, and submit the eligibility file as a request to API gateway server 36, for example, as described in FIG. 8. API gateway server 36 may rely on authentication performed by file transfer server 38 and forward the file to message broker 42. Message broker 42 queues the file for file transfer micro service 44d and sends when micro service 44d becomes available.

Micro service 44d processes the file to create records for the new member. In processing the file, micro service 44d sends a number of messages to portfolio management micro service 44a via message broker 42 to prompt portfolio management micro service 44a to create records for the new member. In processing the messages, portfolio management micro service 44a sends one or more messages to data management micro service 44b, via messages broker 42, to request data be added to data servers 50.

In processing the file, micro service 44d also sends a number of messages using message broker 42 to business management micro service 44d (or third party software platform) to provision a new smart card 16 for the member, send a welcome email to the new member, and/or mail new member documents to the new member's address along with the smart card 16. In the email and/or new member documents, the member is invited to use a web portal for members (provided by front end server 24) to activate the new card.

When the member logs into the member portal, front end server 24 provides log in information to API gateway server 36. API gateway server 36, authenticates the user with authentication server 34. Upon successful authentication, API gateway server 36 provides an authentication token to front end system for use to authenticate subsequent messages that are send to API gateway server 36 to request actions requested by user via the member portal.

After logging in, the web portal may prompt the new member to accepting terms and conditions; provide a profile picture; set up multi-factor authentication for the member and adult dependents; providing voluntary medical history; providing medication history; providing allergies and emergency contact information and/or set up preferences. In response to the member providing information, front end server 24 sends one or more messages to API gateway server to request the information by added to back end system 30. The previously provided authentication token is include in the message sent to the API gateway server 36. The API gateway server 36 uses the token to authenticate the message with authentication server 34. In response to successfully authenticating the message, API gateway server 36 forwards the message to messages broker 42. Message broker queues the message for processing by portfolio management micro service 44a and sends the messages when portfolio management micro service 44a is available. In processing the messages, portfolio management micro service 44a sends one or more messages to data management micro service 44b, via messages broker 42, to request data be added to data servers 50.

Various blocks, modules, or other circuits may be implemented to carry out one or more of the operations and activities described herein and/or shown in the figures. In these contexts, a "block" (also sometimes "logic circuit", "control circuit," "processing circuit," "server," "module," or "system") is a circuit specifically configured and arranged to carry out one or more of these or related operations/activities. For example, such circuits may be discreet logic circuits or programmable logic circuits configured and arranged for implementing these operations/activities, as shown in the figures and/or described in the specification. In certain embodiments, such a programmable circuit may include one or more programmable integrated circuits (e.g., field programmable gate arrays and/or programmable ICs). Additionally or alternatively, such a programmable circuit may include one or more processing circuits (e.g., a computer, microcontroller, system-on-chip, smart phone, server, and/or cloud computing resources). For instance, computer processing circuits may be programmed to execute a set (or sets) of instructions (and/or configuration data). The instructions (and/or configuration data) can be in the form of firmware or software stored in and accessible from a memory (circuit). Certain aspects are directed to a computer program product (e.g., nonvolatile memory device), which includes a machine or computer-readable medium having stored thereon instructions which may be executed by a computer (or other electronic device) to perform these operations/activities.

In various implementations, disclosed blocks, modules, or other circuits, and/or devices may be communicatively connected using any number of communication protocols over various data networks and/or data buses, which may include but are not limited to, for example, 802.3, 802.11/Wi-Fi, Wi-Max, GSM/EDGE, UMTS/HSPA+/HSDPA, CDMA, LTE, Bluetooth, Bluetooth Low Energy, UltraWideband (UWB), ZigBee, Zwave, and/or FM/VHF/UHF networks, PCI, PCIe, SCSI, USB, Hypertransport, or any other communication medium and/or protocol.

From the above discussion it will be appreciated that the system 10 improves upon the state of the art. Specifically, various embodiments provide an improved system for storing, processing, and assessing data related to medical services; a system that is interoperable with third party systems, a system that facilitates transparency, security and verifiability of data; a system that improves efficiency in storage and processing of data and transactions; a system that utilizes a smart card to facilitate identification, authentication, and approvals; a system that is strong, robust, durable, and fault tolerant; a system that can be used in many applications; a system that provides unique functionality; a system that facilitates fast processing of data and transactions; a system that is scalable; a system that is distributed; a system that is easy and intuitive to use; a system that saves time; and a system that improves a user experience.

It will be appreciated by those skilled in the art that other various modifications could be made to the device without parting from the spirit and scope of this disclosure. All such modifications and changes fall within the scope of the claims and are intended to be covered thereby.

What is claimed:

1. A system for storage, processing, and accessing of data, comprising:
a front end system, the front end system including one or more front end servers;
wherein the one or more front end servers are configured to provide a first user interface configured to provide a healthcare provider access to medical and drug history data for a patient when authorized;
wherein the one or more front end servers are configured to provide a second user interface configured to permit the patient to set permissions for access to medical and drug history data for the patient by healthcare providers;
the patient having a smartcard;
a back end system communicatively connected to the front end system;
wherein the back end system includes one or more data servers;
wherein the one or more data servers store the medical and drug history data for the patient;
wherein the front end system includes a card reader;
wherein in response to scanning the smartcard of patient via the card reader, the front end system is configured to authenticate the patient and the healthcare provider;
wherein in response to successful authentication, the front end system is provided an authentication token for the healthcare provider;
wherein in response to user input by the healthcare provider via the first user interface, the front end system is configured to retrieve the medical and drug history data of the patient from the back end system by communicating a request message to the back end system;
wherein the request message includes the authentication token;
wherein the authentication token is indicative of resources the health are provider is permitted to access;
wherein in response to receiving the request message, the back end system is configured to examine the identification token to determine if the health care provider is permitted to access the medical and drug history data;
wherein in response to determining the health care provider is permitted to access the medial and drug history data, the back end system is configured to communicate the medical and drug history data to the front end system to facilitate providing of medical services.

2. The system of claim 1, upon successful authentication, the front end system is further configured to retrieve information of a health insurance policy of the patient.

3. The system of claim 1, upon successful authentication, the front end system is further configured to verify validity of a health insurance policy of the patient.

4. The system of claim 1, wherein the back end system includes one or more interface servers communicatively connected to the one or more data servers;
wherein the back end system includes one or more processing servers communicatively connected to the one or more data servers;
wherein the one or more processing servers are configured to access data in the one or more data servers and perform one or more operations in response to receiving messages from the one or more front end servers; and
wherein the one or more interface servers are configured to operates as a gateway between the front end system, and the one or more processing servers.

5. The system of claim 1, wherein in authenticating the patient using the smartcard, the first user interface prompts the patient to enter a personal identification number, wherein the backend system is configured to authenticate the patient using the smartcard and the personal identification number.

6. The system of claim 1, wherein the first user interface is further configured to facilitate submission of pre-approval requests for procedures to be provided to the patient.

7. The system of claim 1, wherein the system is configured to permit the patient to use the smartcard to for payment of medical services provided to the patient by scanning the smartcard with the card reader;
wherein in response to the patient scanning the smartcard for payment, the system is configured to debit payment from a healthcare savings account, bank account, or other payment system linked to the smartcard in the one or more data servers.

8. A system for storage, processing, and accessing of data, comprising:
a front end system, the front end system including one or more front end servers;
wherein the one or more front end servers are configured to provide a user interface configured to provide a healthcare provider access to medical history data for a patient when authorized;
the patient having a smartcard;
a back end system communicatively connected to the front end system;
wherein the back end system includes one or more data servers;
wherein the one or more data servers store the medical history data for the patient;
wherein the front end system includes a card reader;
wherein in response to scanning the smartcard of patient via the card reader, the front end system is configured to authenticate the patient and the healthcare provider;
wherein in response to successful authentication, the front end system is configured to retrieve the medical history data of the patient from the back end system and provide the healthcare provider access to the medical history data to facilitate providing of medical services;
wherein the first user interface is configured to, in response to user input, store, process, and access data in the one or more data servers by sending messages to the back end system;
wherein the back end system includes one or more interface servers communicatively connected to the one or more data servers;
wherein the back end system includes one or more processing servers communicatively connected to the one or more data servers;
wherein the one or more processing servers are configured to access data in the one or more data servers and perform one or more operations in response to receiving the messages;
wherein the one or more interface servers are configured to operates as a gateway between the front end system, and the one or more processing servers;
wherein the one or more interface servers includes an application program interface (API) server; and
wherein the API server is configured to:
receive the messages from the front end system;
attempt to authenticate the received messages;
forward ones of the authenticated messages that pass authentication to the one or more processing servers; and discard ones of the authenticated messages that fail authentication wherein the front end system includes a plurality of servers configured to communicate with the API server, and an incompatible server that is not capable of communicating with the API server;

wherein the one or more interface servers includes a file transfer server;

wherein the file transfer server is configured to receive files from the incompatible server using a file transfer protocol;

wherein in response to receiving a file from the front end system, the file transfer server is configured to:

determine a sender of the file;

retrieve a file format corresponding to the sender from a memory; and submit the file to the API server as a message in response to determining the file complies with the retrieved file format.

9. The system of claim 8, wherein the messages include a plurality of different types of messages;

wherein the one or more processing servers are configured to provide a plurality of micro services; and wherein each of the micro services is configured to process a subset of the different types of messages.

10. The system of claim 8, wherein the messages include a plurality of different types of messages;

wherein the one or more processing servers are configured to provide a plurality of micro services;

wherein each of the micro services is configured to process a subset of the different types of messages;

wherein the plurality of micro services includes a first micro service configured to process messages requesting changes to health care plan portfolios;

wherein the plurality of micro services includes a second micro service configured to process messages requesting access to one or more data servers; and wherein the plurality of micro services includes a third micro service configured to process messages requesting setup of a new group health care plan.

11. The system of claim 8, wherein the messages include a plurality of different types of messages;

wherein the one or more processing servers are configured to provide a plurality of micro services; and wherein each of the plurality of micro services is configured to process a subset of the different types of messages;

wherein the one or more processing servers includes a message broker;

wherein the message broker includes respective queue for each of the plurality of micro services;

wherein the message broker is configured to receive the messages from the front end system and place each message in the respective queue of the micro service configured to process the message; and wherein the message broker is configured to, in response to one micro service of the plurality of micro services becoming available and the respective queue for the micro service including a message, forward the message to the micro service.

12. A system for storage, processing, and accessing of data, comprising:

a front end system, the front end system including a first set of one or more processing circuits;

wherein the first set of one or more processing circuits is configured to provide one or more front end servers;

wherein the one or more front end servers are configured to provide one or more user interfaces;

a back end system communicatively connected to the front end system;

wherein the back end system includes one or more data servers;

wherein the user interfaces are configured to, in response to user input, store, process, and access data in the one or more data servers by sending messages to the back end system;

wherein the back end system includes a second set of one or more processing circuits;

wherein the second set of one or more processing circuits is configured to provide one or more interface servers communicatively connected to the one or more data servers;

wherein the back end system includes one or more processing servers communicatively connected to the one or more data servers;

wherein the one or more processing servers are configured to access data in the one or more data servers and perform one or more operations in response to receiving the messages;

wherein the one or more interface servers are configured to operate as a gateway between the front end system, and the one or more processing servers;

wherein the one or more interface servers includes an application program interface (API) server; and wherein the API server is configured to:

receive the messages from the front end system;

attempt to authenticate the received messages;

forward ones of the authenticated messages that pass authentication to the one or more processing servers; and discard ones of the authenticated messages that fail authentication wherein the front end system includes a plurality of servers configured to communicate with the API server, and an incompatible server that is not capable of communicating with the API server;

wherein the one or more interface servers includes a file transfer server;

wherein the file transfer server is configured to receive files from the incompatible server using a file transfer protocol;

wherein in response to receiving a file from the front end system, the file transfer server is configured to:

determine a sender of the file;

retrieve a file format corresponding to the sender from a memory; and submit the file to the API server as a message in response to determining the file complies with the retrieved file format.

13. The system of claim 12, wherein the messages include a plurality of different types of messages;

wherein the one or more processing servers are configured to provide a plurality of micro services; and wherein each of the micro services is configured to process a subset of the different types of messages.

14. The system of claim 12, wherein the plurality of micro services includes a first micro service configured to process messages requesting changes to health care plan portfolios;

wherein the plurality of micro services includes a second micro service configured to process messages requesting access to one or more data servers; and wherein the plurality of micro services includes a third micro service configured to process messages requesting setup of a new group health care plan.

15. The system of claim 12, wherein the one or more processing servers includes a message broker;

wherein the one or more processing servers are configured to provide a plurality of micro services;

wherein the message broker includes respective queue for each of the plurality of micro services;

wherein the message broker is configured to receive the messages from the front end system and place each message in the respective queue of the micro service configured to process the message; and wherein the message broker is configured to, in response to one micro service of the plurality of micro services becoming available and the respective queue for the micro service including a message, forward the message to the micro service.

16. The system of claim 12, wherein at least one server configured to communicate with the first interface server is a web server configured to provide a web portal providing at least one user interfaces.

17. The system of claim 12, wherein the front end system includes one or more card readers; and wherein the first interface server is configured to authenticate users of the user interfaces with smart cards using the one or more card readers.

18. The system of claim 12, wherein the first user interface is configured to provide a healthcare provider access to medical history and drug history data for a patient when authorized.

* * * * *